(12) United States Patent
Park et al.

(10) Patent No.: US 8,427,643 B2
(45) Date of Patent: Apr. 23, 2013

(54) REAL-TIME PCR MONITORING APPARATUS

(75) Inventors: Hanee Park, Daejeon (KR); Il kyu Choi, Chungbuk (KR); Han Oh Park, Daejeon (KR)

(73) Assignee: Bioneer Corporation, Daejeon (KR)

( * ) Notice: Subject to any disclaimer, the term of this patent is extended or adjusted under 35 U.S.C. 154(b) by 562 days.

(21) Appl. No.: 12/598,061

(22) PCT Filed: Jun. 17, 2008

(86) PCT No.: PCT/KR2008/003408
§ 371 (c)(1), (2), (4) Date: Oct. 29, 2009

(87) PCT Pub. No.: WO2009/002034
PCT Pub. Date: Dec. 31, 2008

(65) Prior Publication Data
US 2010/0085570 A1   Apr. 8, 2010

(30) Foreign Application Priority Data
Jun. 28, 2007  (KR) .................. 10-2007-006-4558

(51) Int. Cl.
*G01J 4/00* (2006.01)
(52) U.S. Cl.
USPC .......................................................... 356/364
(58) Field of Classification Search .................. 356/317, 356/318, 417, 364–370, 322, 327; 250/458.1–461.2; 422/82.07–82.08; 436/172; 600/317
See application file for complete search history.

(56) References Cited

U.S. PATENT DOCUMENTS

| | | | |
|---|---|---|---|
| 5,943,129 A | 8/1999 | Hoyt et al. | |
| 6,359,284 B1 | 3/2002 | Hayashi et al. | |
| 6,818,437 B1 | 11/2004 | Gambini et al. | |
| 2003/0219754 A1 | 11/2003 | Oleksy et al. | |
| 2006/0192960 A1 | 8/2006 | Rencs et al. | |
| 2007/0114444 A1 | 5/2007 | Reid et al. | |
| 2008/0212090 A1* | 9/2008 | Lee et al. | 356/317 |

FOREIGN PATENT DOCUMENTS

| | | |
|---|---|---|
| CN | 1664562 | 9/2005 |
| CN | 1798969 | 7/2006 |
| EP | 0 640 828 | 3/1995 |

(Continued)

OTHER PUBLICATIONS

B. Crane et al., "Towards Fluorescence Anisotropy Detection for Real-Time PCR Assays", Proceedings of the 25th Annual International Conference of the IEEE EMBS, Cancun, Mexico, Sep. 17-21, 2003, © 2003 IEEE, pp. 3060-3063.

(Continued)

*Primary Examiner* — Gregory J Toatley
*Assistant Examiner* — Rufus Phillips
(74) *Attorney, Agent, or Firm* — Clark & Brody

(57) ABSTRACT

The present invention relates to a real-time PCR monitoring apparatus for real-time monitoring production of reaction product produced during the reaction while performing nucleic acid amplification such as PCR for various kinds of trace samples. Specifically, the present invention relates to an apparatus for real-time monitoring biochemical reaction for efficiently dividing interference between an excitation light and a fluorescence, which includes a polarizer, a polarizing beam splitter, a polarization converter and so on.

3 Claims, 4 Drawing Sheets

FOREIGN PATENT DOCUMENTS

| | | |
|---|---|---|
| JP | 2003-524754 | 8/2003 |
| JP | 2005-195582 | 7/2005 |
| JP | 2006-522330 | 9/2006 |
| KR | 2003-0096877 | 12/2003 |
| KR | 10-2006-0009246 | 1/2006 |
| WO | 2004/088291 | 10/2004 |

OTHER PUBLICATIONS

M. Schäferling et al., "Optical technologies for the read out and quality control of DNA and protein microarrays", *Anal. Bioanal. Chem.* (2006) 385: 500-517.

* cited by examiner

REAL-TIME PCR MONITORING APPARATUS

TECHNICAL FIELD

The present invention relates to a real-time polymerase chain reaction (PCR) monitoring apparatus, and more particularly, to a real-time PCR monitoring apparatus for real-time monitoring of reaction product produced during the reaction while performing nucleic acid amplification such as PCR for various kinds of trace samples.

BACKGROUND ART

In recent, there has been developed a real-time PCR technology that can real-time monitor a reaction product during PCR process. With this technology, it is not necessary to perform an electrophoresis on gel and it is possible to confirm the amplified product during the reaction cycle as well as to obtain a quantitative result. In order to perform this real-time PCR, an apparatus incorporated with a thermal cycler for the PCR reaction and a fluorometer for the real-time detection of reactant is used.

In general, a fluorescent detection using a fluorescent reagent is used to monitor the real-time PCR, typical methods includes the followings:

1) Intercalating method: an Intercalator (for example, SYBR Green I, EtBr, etc.), i.e. a reagent that shows fluorescence by binding with double strand DNA is added to a reaction system and fluorescence generated with amplification is detected. That is to say, fluorescence is generated when an Intercalator is bound with double strand DNA synthesized through the PCR and it is possible to measure quantity as well as melting temperature of the amplified DNA by detecting the fluorescent intensity.

2) TaqMan™ probe method: oligonucleotide in which 5' terminal is modified to fluorescent material (e.g. FAM, etc.) and 3' terminal is modified to quencher material (e.g. TAMRA, etc.) is added. Under an annealing condition, TaqMan™ probe is specifically hybridized with a template DNA, but fluorescence is blocked by the quencher. During an amplification reaction, fluorescence generated as the template is digested by 5'-3' exonuclease activity of the Taq DNA polymerase and then the blocking by capture is released.

3) Molecular Beacon method: oligonucleotide (Molecular Beacon probe) that forms a secondary hairpin structure in which both ends thereof are modified to fluorescent material (e.g. FAM, TAMRA, etc.) and quencher material (e.g. DABCYL, etc.) is added to the reaction. The Molecular Beacon probe is specifically hybridized with a complementary region to a template under an annealing condition. At this time, fluorescence generated as a distance between the fluorescent dye and the quencher becomes more distant and the blocking by the quencher is thus released. Meanwhile, unhybridized Molecular Beacon probe does not generate the fluorescence since it has a secondary structure and is thus blocked by the quencher.

A conventional apparatus for real-time PCR (U.S. Pat. No. 6,818,437) includes, as shown in FIG. 1, a thermoelectric element 1c, a block 1 for transferring heat to reaction tubes 2a containing a sample, a light source 11 for irradiating a beam into the sample contained in the reaction tube and a sensor part 78 for receiving fluorescence generated from the sample. The principle of the aforementioned apparatus is as follows: in order to react nucleic sample solution within the tube, a cooling and heating cycle is repeatedly performed using the thermoelectric element 1c; and upon completion of each cycle, an intensity of the fluorescence generated from the sample is measured by the operation of the light source 11 and the sensor part 78, thereby checking the progress of the reaction in real-time. The light source 11 is a white light source, and a band pass filter 7 is used in order to generate an excitation light having a frequency corresponding to that of the used fluorescent probe. A dichroic beam splitter 6 is a device for separating the excitation light and the fluorescence. In FIG. 1, it reflects light having a frequency lower than a specific frequency and passes light having a frequency higher than the specific frequency. Another band pass filter 8 is for selectively passing only the fluorescence emitted from the sample to the sensor part 78. In addition, a Fresnel lens 3 is used for parallelizing the excitation light.

In recent, there has been introduced a real-time PCR experiment in which fluorescent probes of various colors are used at the same time. However, in the conventional technology, different dichroic beam splitters are required according to the fluorescent probe if the frequencies of the used fluorescent probes are different. Therefore, in the conventional technology, the band pass filters 7 and 8 and the dichroic beam splitters 6 are incorporated into a single module, and data is obtained while changing the module according to the fluorescent probe. For example, if five kinds of band pass filters are used, five kinds of dichroic beam splitters are required to match the band pass filters.

Also, in the case of the dichroic beam splitter used in the conventional technology, since the excitation light is generally brighter $10^5$ times then the fluorescence generated from the sample, it is impossible to completely separate the excitation light and the fluorescence. Further, a reflection light of the excitation light by an optical component on the light path is incident to the fluorescence detecting part and interferes with the fluorescence generated from the sample.

The factor that causes the reflection of the excitation light includes:

1) the Fresnel lens 3 used to parallelize the excitation light, 2) a lid 2b or a transparent tape used to prevent vaporization of the sample in the reaction tube 2a and 3) the reaction tube itself.

DISCLOSURE

Technical Problem

An object of the present invention is to separate an excitation light and a fluorescence regardless of frequency and prevent reflection light of the excitation light from being incident to a fluorescence detecting part without using a dichroic beam splitter that is conventionally used to divide the excitation light and the fluorescence, by causing the excitation light and the fluorescence to have polarization components of different directions from each other using polarization properties of light.

Technical Solution

The real-time polymerase chain reaction (PCR) monitoring apparatus includes a polarization converter (102) for converting the excitation light excited from a light source (100); a condensing lens (103) for condensing the polarized light converted from the polarization converter (102); a light tunnel (104) converting and transferring the polarized light condensed by the condensing lens (103) into a uniform surface light; a first band pass filter (105) for allowing a polarized light with a specific frequency of the surface light transferred from the light tunnel (104) that is matched with excitation properties of a fluorescent probe, to pass therethrough; a polarizing beam splitter (108) for separating the polarized light with a specific frequency passed through band pass filter (105); a surface mirror (109) for transferring the polarized light separated in a specific direction from the polarizing beam splitter (108) to a sample, and reflecting the fluorescence generated from the sample to the polarizing beam splitter (108); a first polarizer (111) for polarizing the excitation light so that the fluorescence reflected by the surface mirror (109) has the same component as the polarized light transferred to the polarizing beam splitter (108), at which only polarization component with different direction from the excitation light is reflected and transferred to a fluorescence detecting lens (113), and converted by the polarization converter (102); and a fluorescence detecting lens (113) for receiving the fluorescence generated from the sample.

The PCR monitoring apparatus may further include a second polarizer (107) for polarizing the fluorescence so as to have the opposite component to the polarization converter (102) and the first polarizer (111) for preventing the polarized excitation light from being reflected and incident to the fluorescence detecting part.

The PCR monitoring apparatus may further include a second band pass filter (112) for allowing a light with a specific frequency of the fluorescence, generated from the polarized excitation light passed through the first polarizer (111), that is matched with an emitting properties of the fluorescent probe, to pass therethrough.

The PCR monitoring apparatus may further include a ultraviolet ray (UV) and infrared ray (IR) cut-off filter (101) provided between the light source (100) and the polarization converter (102) to cut off the CV and IR.

The PCR monitoring apparatus may further include a sample vessel for containing the sample.

The sample vessel is preferably any one selected from a vessel provided with tubes or multi-well plate, a Petri dish, a slide, a Terasaki plate, or a PCR plate.

DESCRIPTION OF DRAWINGS

The above and other objects, features and advantages of the present invention will become apparent from the following description of preferred embodiments given in conjunction with the accompanying drawings, in which.

DETAILED DESCRIPTION OF MAIN ELEMENTS

Figure 1:
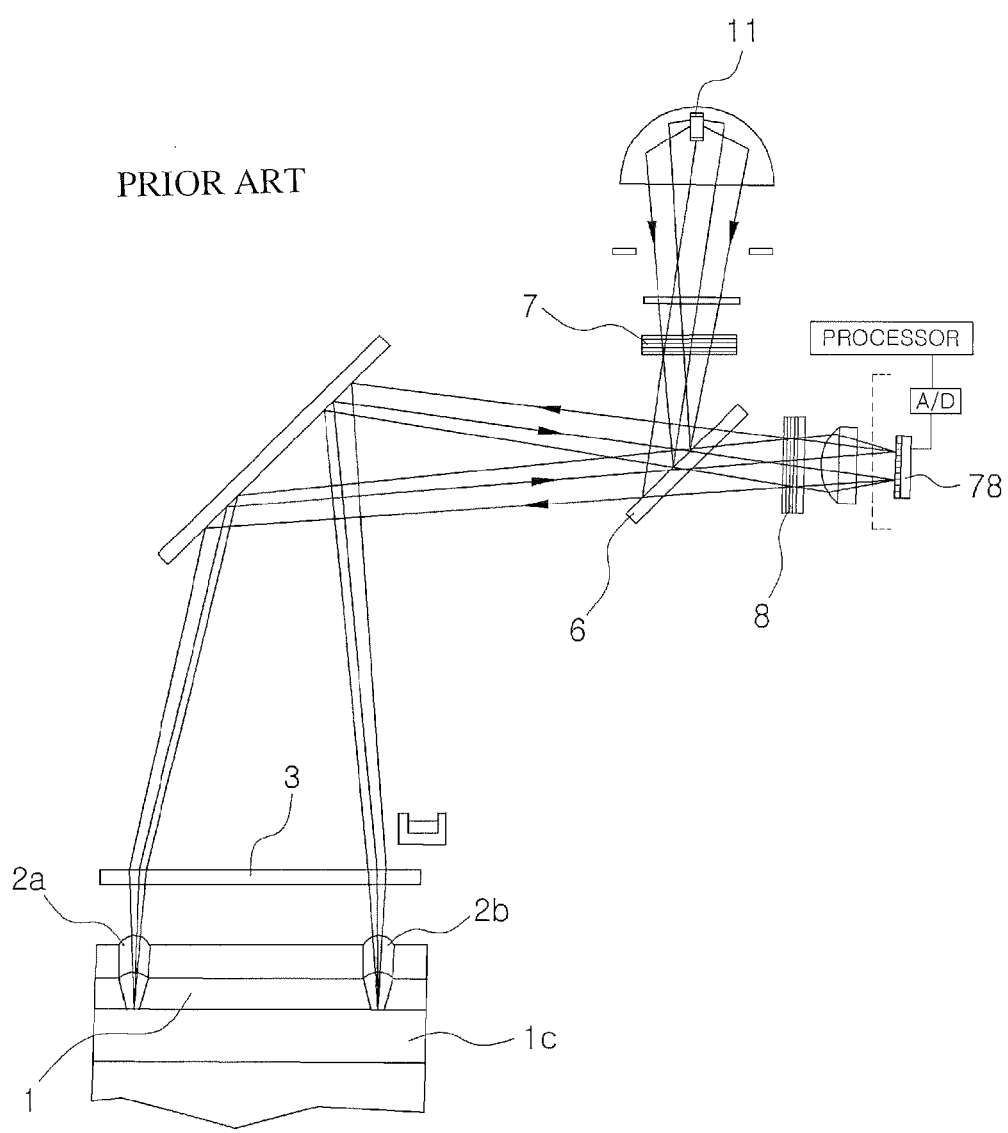
FIG. 1 is a view illustrating a conventional real-time PCR monitoring apparatus.

100: light source
101: UV and IR cut-off filter
102: polarization converter
103: condensing lens
104: light tunnel
105: first band pass filter
106: focusing lens
107: second polarizer
108: polarizing beam splitter
109: surface mirror
110: Fresnel lens
111: first polarizer
112: second band pass filter
113: fluorescence detecting lens

BEST MODE

Hereinafter, the embodiments of the present invention will be described in detail with reference to accompanying drawings.

The present invention provides an apparatus for effectively separating an excitation light and a fluorescence from a sample using polarization properties of light.

Figure 2:
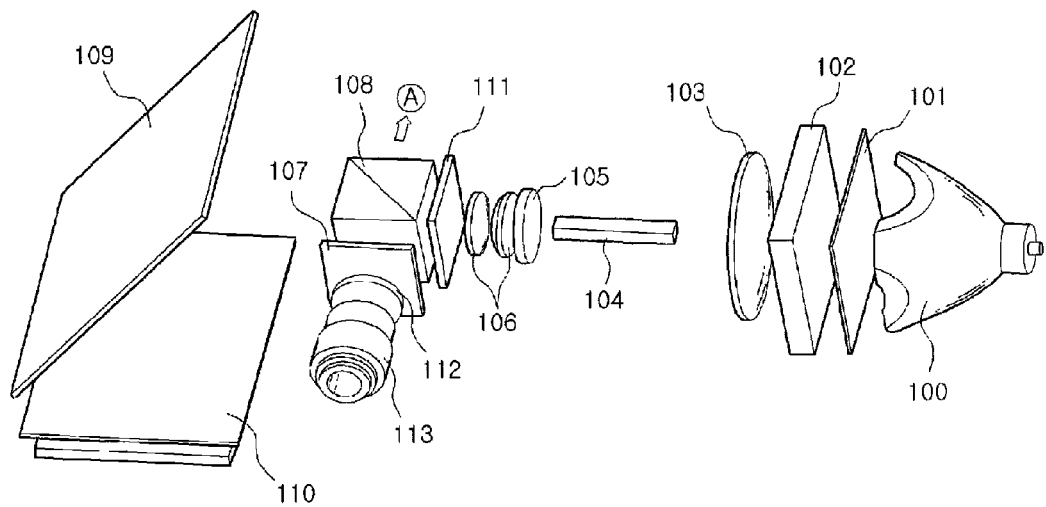
FIG. 2 is a perspective view illustrating a real-time PCR monitoring apparatus according to an embodiment of the present invention.
Figure 3:
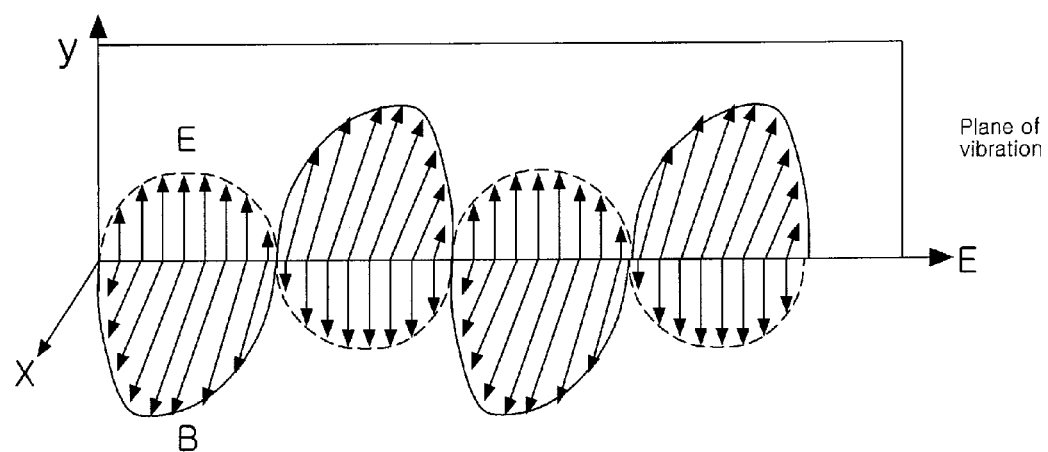
FIG. 3 is a view illustrating polarization properties of light.
Figure 4:
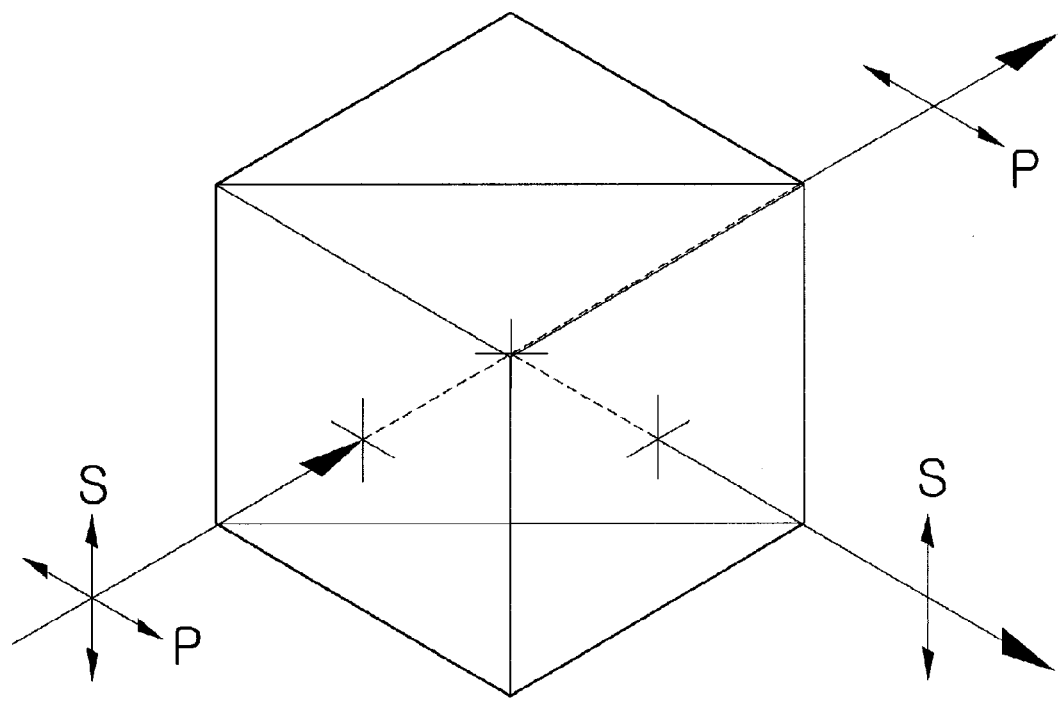
FIG. 4 is a view illustrating polarization properties of a polarizing beam splitter.
Figure 5:
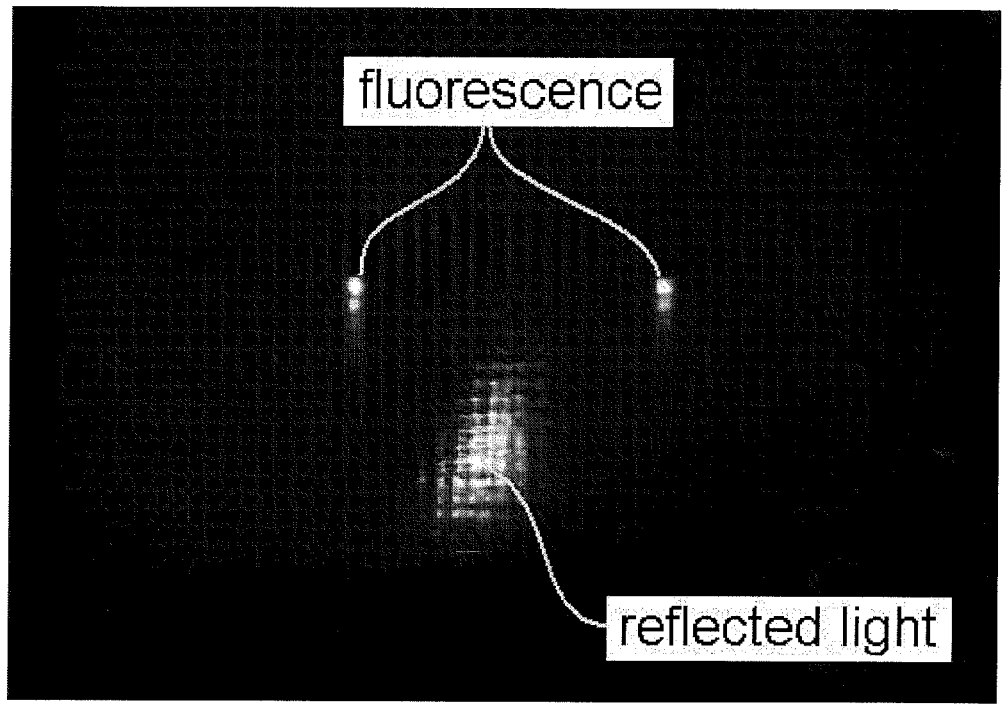
FIG. 5 is a photograph taking a reaction tube (plate) from a fluorescence detecting part when using a non-polarization optical system.
Figure 6:
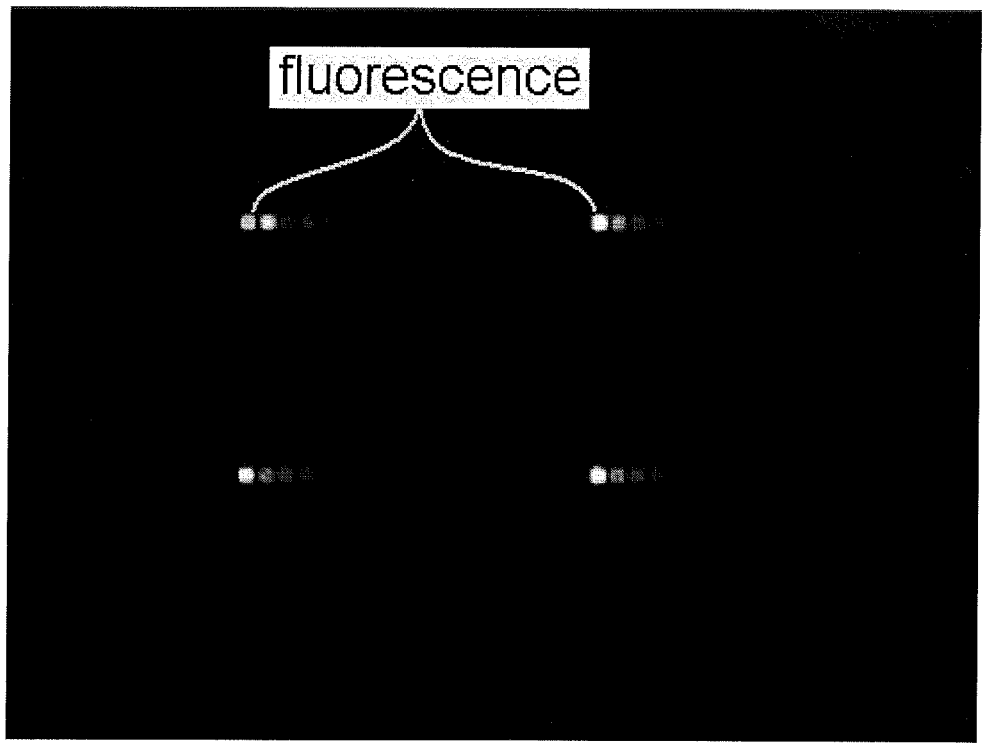
FIG. 6 is a photograph taking a reaction tube (plate) from a fluorescence detecting part when using an optical system according to an embodiment of the present invention.

FIG. 2 is a perspective view illustrating a real-time PCR monitoring apparatus according to an embodiment of the present invention; FIG. 3 is a view illustrating polarization properties of light beam; FIG. 4 is a view illustrating polarization properties of a polarizing beam splitter; FIG. 5 is a photograph taking a reaction tube (plate) from a fluorescence detecting part when using a non-polarization optical system; and FIG. 6 is a photograph taking a reaction tube (plate) from a fluorescence detecting part when using an optical system according to an embodiment of the present invention.

As shown, the real-time PCR monitoring apparatus according to an embodiment of the present invention includes a polarization converter 102 for polarizing an excitation light excited from the light source 100; a condensing lens 103 for condensing the polarized light converted from the polarization converter 102; a light tunnel 104 for making the polarized light condensed by the condensing lens 103 to uniform surface light; a first band pass filter 105 passing the polarized light transferred from the light tunnel 104; a polarizing beam splitter 108 separating the polarized light passed through the first band pass filter 105 from fluorescence; a surface mirror 109 for transferring the polarized light with the specific direction to a sample and reflecting a fluorescence generated from the sample; a second polarizer for polarizing the fluorescence reflected by the surface mirror 109; a second band pass filter 112 for allowing only a fluorescence with a specific frequency of the fluorescence transferred from the second polarizer that is matched with the properties of a fluorescent probe, to pass therethrough; and a fluorescence detecting lens 113 for receiving the fluorescence passed through the second band pass filter 112.

The real-time PCR monitoring according to the present invention employs a fluorescent detection using a fluorescent reagent disclosed in Korean Patent Laid Open 10-2006-0009246 (title: apparatus for real-time monitoring biochemical reaction) by the present inventor.

Examples of the light source 100 may include a white light source such as a tungsten-halogen lamp, a xenon discharge lamp, etc. and a monochromatic light source such as a laser, etc. In case of a specific laser, the laser itself emits a polarized light.

The light emitted from the light source 100 for generating the excitation light has properties of a parallel light and characteristics of a non-polarized light. This light has both S-wave and P-wave components as shown in FIG. 4. In other words, the light is constituted of the S-wave and the P-wave perpendicular to each other with respect to a proceeding direction.

The light emitted from the light source 100 has generally components of visible lays as well as ultraviolet ray (UV) and infrared ray (IR). Therefore, in order to remove the UV and IR components that are not necessary to the optical system, it is preferable to provide an UV and IR cut-off filter 101 to remove the UV and IR components.

The polarization converter 102 serves to convert the excitation light to have the same polarity with respect to a specific direction. In other words, the polarization converter 102 serves to convert the incident non-polarized beam to have a single polarity. The reason for using the polarization converter 102 is because: since entire light intensity is reduced to less than 50% when removing one polarity to obtain only the other polarity from the light constituted of S-wave and P-wave, it is possible to raise a using efficiency of the light by converting the polarity component to be removed into the polarity component that is matched with the using object.

The condensing lens 103 condenses the polarized light converted from the polarization converter 102, so that the converted polarized light is incident to the light tunnel 104 having a small size.

The light tunnel 104 is used as a means for generating uniform surface light as disclosed in WO2004/088291.

The first band pass filter 105 allows only the polarized excitation light with a specific frequency of the polarized excitation light transferred from the light tunnel 104, which matches with excitation properties of the fluorescent probe, to pass therethrough.

The present invention improves the conventional problems in that when using various kinds of fluorescent probes, different band pass filter should be used according to each fluorescent probes and thus different kinds of dichroic beam splitters (refer numeral 6 in FIG. 1) should be used (for example, five sets of band pass filter require also five dichroic beam splitters), and thus can separate the fluorescence and the excitation light without using the dichroic beam splitter.

The polarizing beam splitter 108 is an optical part that separate non-polarized light incident thereto into light having one polarization component and light having the rest polarization components with an angle of 90 degrees therebetween. In other words, in FIG. 2, the non-polarized excitation light is separated in Ⓐ direction.

The polarizing beam splitter 108 divides the excitation light of the specific frequency passed through the first band pass filter 105 into respective polarization components.

The polarized light separated by the polarizing beam splitter 108 is transferred to the surface mirror 109, and the rest of the polarized light are separated from a opposite direction to the fluorescence detecting lens 113, i.e. in Ⓐ direction.

In the present invention, it is assumed for explanation that the polarization converter 102 converts the non-polarized beam into S-wave. Of course, the same effect can be obtained by adjusting angles of the polarizer and the polarization converter even when the non-polarized beam is converted into P-wave.

Therefore, S-wave of the excitation light components passes through the polarizing beam splitter 108, and P-wave is reflected at the polarizing beam splitter 108 and incident in Ⓐ direction. Accordingly, only the excitation light of S-wave component is transferred to the sample through the surface mirror 109.

At this time, it is preferable that a sample vessel for containing the sample is further provided.

The sample vessel is preferably any one selected from a vessel provided with tubes or multi-well plate, a Petri dish, a slide, a Terasaki plate, a PCR plate, but any sample vessel that can contain and measure the sample can be used.

Further, it is preferable that a focusing lens 106 for generating a uniform surface light corresponding to the size of the sample vessel containing the sample is provided between the first band pass filter 105 and the polarizing beam splitter 108. The focusing lens 106 spreads the excitation light so that the intensity of the excitation light is uniform when the excitation light arrives at the tube (plate) containing the sample of which fluorescence is to be detected.

The surface mirror 109 transfers the separated polarized light from the polarizing beam splitter 108 to the sample, and reflects the fluorescence generated from the sample to the polarizing beam splitter 108. In other words, the surface mirror 109 merely serves to change the light path.

Fresnel lens 110 is used to make the excitation light reflected by the surface mirror 109 to a parallel light so that the light arrives well to the tube containing the sample. The resulting incident excitation light causes the fluorescent probe to be excited and thus emit the fluorescence. The fluorescence generated at the sample is incident to the fluorescence detecting part through the Fresnel lens and the polarizing beam splitter.

The first polarizer 111 serves to maximally remove polarization components of unnecessary directions before the excitation light is incident to the polarizing beam splitter 108 since the polarization properties of the excitation light may be distracted when the excitation light polarized by the polarization converter 102 passes through optical parts (i.e. condensing lens 103, light tunnel 104, the focusing lens 106, etc.). In other words, first polarizer 111 serves to remove slight P-wave component generable by distraction of the polarized light during the polarized excitation light of S-wave component passes through the light path.

The fluorescence generated from the sample also has characteristics of a non-polarized light and thus has both S-wave and P-wave components. When the fluorescence with this characteristic is incident to the polarizing beam splitter 108 as shown in FIG. 4, the P-wave is reflected and then inputted into the fluorescence detecting lens 113 and the S-wave passes through the polarizing beam splitter 108 and then is incident to the excitation light source. The second polarizer 107 is the same kind as the first polarizer 111 but is rotated by 90 degree so as to allow only P-wave to pass therethrough. Therefore, the second polarizer 107 serves to remove light of S-wave component that might not be completely removed at the polarizing beam splitter 108.

Herein, even though the excitation light is reflected on the light path and thus is incident to the fluorescence detecting lens 113, due to its characteristic of S-wave, the excitation light is incident again to the excitation light source through the polarizing beam splitter and is also blocked by the second polarizer 107. Therefore, the excitation light cannot be incident to the fluorescence detecting lens 113.

The fluorescence reflected to the surface mirror 109 is transferred to the polarizing beam splitter 108 and comes to have the opposite component to the polarized light converted by the first polarizer 111 and the polarization converter 102. In other words, the excitation light and the fluorescence have different polarities from each other. Therefore, the fluorescence can be effectively separated as the interference of the excitation light cannot have an influence on the fluorescence.

As described above, in the present invention, it is possible to effectively remove excitation light by causing the excitation light to have single polarization component, and removing the single polarization component and passing the rest polarization components to transfer the rest polarization components to a fluorescence detecting sensor, at the fluorescence detecting part collecting the fluorescence outputted from the sample.

The second band pass filter 112 passes only fluorescence having specific frequency of the polarized fluorescence transferred from the second polarizer 107 so as to match with the emitting properties of the fluorescent probe.

The fluorescence detecting lens 113 receives the fluorescence passed through the second band pass filter 112 and is provided with the fluorescent probe (not shown) to collect the fluorescence from the sample. The lens 113 focuses the fluorescence generated from the sample to an image sensor.

Preferably, the real-time PCR monitoring apparatus of the present invention is further provided with a first polarizer 111 for polarizing the excitation that is not converted by the polarization converter 102. Since the polarization characteristics can be broken down during the polarized light passes through optical parts, the first polarizer 111 serves to maintain the polarization characteristics as a pre-polarizer that is used prior to the polarizing beam splitter 108 in order to raise the beam separating efficiency of the polarizing beam splitter 108.

In addition, the real-time PCR monitoring apparatus of the present invention may further includes UV and IR cut-off filter 101 provided between the light source 100 and the polarization converter 102 and cut off the UV and IR.

The present invention is characterized in that the excitation light and the fluorescence have different polarization characteristics from each other and thus interference of the excitation light on the fluorescence is minimized so as to prevent the excitation light from being reflected by a specific optical part on the light path, a lid (refer to 2b in FIG. 1) or a transparent tape used to prevent vaporization of the sample, the reaction tube (refer to 2a in FIG. 1) or the like and being incident to the fluorescence detecting part. Since the reflected polarized light still has the same polarization characteristics, it is possible to efficiently divide the excitation light and the fluorescence.

FIG. 5 is a photograph taking a reaction tube (plate) from a fluorescence detecting part when using a non-polarization optical system. In this photograph, wells containing the fluorescent probe are shown at left and right sides of the middle and brightness by reflected light is shown across several wells in the middle.

FIG. 6 is a photograph taking a reaction tube (plate) from a fluorescence detecting part when using an optical system according to an embodiment of the present invention. As shown, reflected light at the lower middle portion was completely disappeared.

INDUSTRIAL APPLICABILITY

In the conventional real-time PCR monitoring apparatus, it is impossible to collect only fluorescence generated from the sample since the excitation light is reflected by an optical part laid on the light path (for example, a Fresnel lens, a glass heater or the like), a lid or a transparent tape used to prevent vaporization of the sample, the reaction tube or the like and then is incident to the fluorescence detecting part. When processing massive samples, amount of the sample is reduced and thus the amount of the fluorescence generated from the sample is also reduced. This results in more serious problem.

By improving the problem of the interference due to the excitation light, the real-time PCR monitoring apparatus of the present invention has an advantage that the excitation light and the fluorescence have different polarities from each other and thus the interference of the excitation light cannot have an influence on the fluorescence. Also, in the real-time PCR monitoring apparatus of the present invention, since it is possible to receive the fluorescence using only one polarizing beam splitter for dividing the excitation light and the fluorescence regardless of the frequency and number of the band pass filter without using a dichroic beam splitter, it is not necessary to install an change a plurality of the dichroic beam splitters and it is not required mechanical components for setting the dichroic beam splitters according to each frequency and thus it is very economy.

The invention claimed is:

1. A real-time polymerase chain reaction (PCR) monitoring apparatus, comprising:
    a condensing lens (103) for condensing an excitation light generated from a light source (100);
    a light tunnel (104) converting and transferring the excitation light condensed by the condensing lens (103) into a uniform surface light;
    a first band pass filter (105) for allowing a polarized light with a specific frequency of the surface light transferred from the light tunnel (104) that is matched with excitation properties of a fluorescent probe, to pass therethrough;
    a first polarizer (111) for polarizing the excitation light with a specific frequency passed through the first band pass filter (105);
    a polarizing beam splitter (108) for separating the polarized light with a specific frequency passed through first polarizer (111);
    a surface mirror (109) for transferring the polarized light divided from the polarizing beam splitter (108) to a sample, and reflecting the fluorescence generated from the sample to transfer the fluorescence to the polarizing beam splitter (108);
    a second polarizer (107) for polarizing the fluorescence so that the fluorescence reflected by the surface mirror (109) has the opposite component to the polarized light transferred to the polarizing beam splitter (108) and converted by the first polarizer (111);
    a second band pass filter (112) for allowing a fluorescence with a specific frequency of the polarized fluorescence transferred from the second polarizer (107) that is matched with an emitting properties of the fluorescent probe, to pass therethrough;
    a fluorescence detecting lens (113) for receiving the fluorescence passed through the second band pass filter (112); and
    a polarization converter (102) for converting the excitation light with a polarization component that would be removed by the first polarizer (111) into the excitation light with the polarization component capable of passing through the first polarizer (111), wherein the polarization converter 102 is provided between the light source 100 and the condensing lens 103.

2. The real-time PCR monitoring apparatus as set forth in claim 1, further comprising:
    a sample vessel for containing the sample.

3. The real-time PCR monitoring apparatus as set forth in claim 2, wherein the sample vessel is any one selected from a vessel provided with tubes or multi-well plate, a Petri dish, a slide, a Terasaki plate, or a PCR plate.

* * * * *